US012773032B2

(12) United States Patent
Jinete

(10) Patent No.: US 12,773,032 B2
(45) Date of Patent: Oct. 27, 2026

(54) THERAPEUTIC SHOE

(71) Applicant: Enrique Carlos Jinete, White Plains, NY (US)

(72) Inventor: Enrique Carlos Jinete, White Plains, NY (US)

( * ) Notice: Subject to any disclaimer, the term of this patent is extended or adjusted under 35 U.S.C. 154(b) by 32 days.

(21) Appl. No.: 18/659,675

(22) Filed: May 9, 2024

(65) Prior Publication Data

US 2024/0341401 A1 Oct. 17, 2024

Related U.S. Application Data

(63) Continuation of application No. 16/948,258, filed on Sep. 10, 2020, now abandoned.

(51) Int. Cl.

| | |
|---|---|
| ***A43B 7/1455*** | (2022.01) |
| ***A43B 3/34*** | (2022.01) |
| ***A43B 7/1475*** | (2022.01) |
| ***A43B 23/22*** | (2006.01) |
| ***A61F 5/14*** | (2022.01) |

(52) U.S. Cl.

CPC ................ *A43B 7/147* (2013.01); *A43B 3/34* (2022.01); *A43B 7/1475* (2013.01); *A43B 23/22* (2013.01); *A61F 5/14* (2013.01)

(58) Field of Classification Search

CPC ......... A61F 5/14; A43B 23/22; A43B 7/1435; A43B 3/34; A43B 7/147

USPC ...................................................... 36/88, 3 A

See application file for complete search history.

(56) References Cited

U.S. PATENT DOCUMENTS

| | | | | |
|---|---|---|---|---|
| 1,240,249 | A | 9/1917 | Peckham | |
| 1,468,363 | A * | 9/1923 | Howe | A43B 17/00 36/44 |
| 1,470,618 | A | 10/1923 | Craine | |
| 2,386,667 | A | 10/1945 | Doherty | |
| 4,440,158 | A | 4/1984 | Shapiro | |
| 4,706,316 | A | 11/1987 | Tanzi | |
| 4,724,847 | A * | 2/1988 | Nelson | A61F 5/0111 602/27 |
| 4,819,644 | A | 4/1989 | Cherniak | |
| 4,936,295 | A | 6/1990 | Crane | |
| 5,951,799 | A | 9/1999 | Williamson et al. | |
| 6,023,857 | A | 2/2000 | Vizy et al. | |

(Continued)

FOREIGN PATENT DOCUMENTS

EP 3120814 A1 1/2017

OTHER PUBLICATIONS

Trott, "Children's foot problems." Orthop Clin North Am., Jul. 1982, Retrieved Aug. 12, 2020, from https://pubmed.ncbi.nlm.nih.gov/7099593/, 1 page.

(Continued)

*Primary Examiner* — Alissa J Tompkins
*Assistant Examiner* — Catherine M Ferreira
(74) *Attorney, Agent, or Firm* — Maier & Maier, PLLC

(57) ABSTRACT

An engineered therapeutic footwear for correcting a biomechanical misalignment and provide proper foot alignment. The therapeutic footwear comes with a built in GPS tracking system. The corrective footwear improves biomechanical foot issues by an inner molded brace that provides medial and lateral support, with internal metal frame support incorporated into the molded brace. The built in GPS is utilized to track the location of a child with/without disabilities and physical activity.

21 Claims, 5 Drawing Sheets

(56) References Cited

U.S. PATENT DOCUMENTS

| | | | | |
|---|---|---|---|---|
| 6,718,656 | B2 | 4/2004 | Houser et al. | |
| 6,788,200 | B1 | 9/2004 | Jamel et al. | |
| 7,069,665 | B1 | 7/2006 | Adriano | |
| 7,077,818 | B2 | 7/2006 | Ingimundarson et al. | |
| 7,618,387 | B2 | 11/2009 | Buethorn | |
| 8,708,942 | B2 * | 4/2014 | Kuhn | A61F 5/0127 602/23 |
| 8,819,961 | B1 | 9/2014 | Ellis | |
| 8,904,674 | B2 | 12/2014 | Schwartz | |
| 9,060,565 | B2 | 6/2015 | Kosta | |
| 9,402,437 | B2 * | 8/2016 | Berns | A43B 5/0405 |
| 9,516,920 | B1 | 12/2016 | Derose | |
| 9,655,405 | B2 | 5/2017 | Hamill | |
| 9,682,003 | B2 | 6/2017 | Gourineni | |
| 10,012,969 | B2 | 7/2018 | Ellis | |
| 10,470,711 | B2 | 11/2019 | Yuan et al. | |
| 2006/0086004 | A1 | 4/2006 | Davis et al. | |
| 2007/0191748 | A1 | 8/2007 | Buethorn | |
| 2009/0139113 | A1 * | 6/2009 | Buethorn | A43B 7/28 36/140 |
| 2010/0319217 | A1 | 12/2010 | Echols | |
| 2011/0196276 | A1 * | 8/2011 | Kuhn | A61F 5/0127 602/27 |
| 2011/0260857 | A1 * | 10/2011 | Hamill | A43B 17/00 12/146 M |
| 2011/0289802 | A1 | 12/2011 | Clough | |
| 2012/0311887 | A1 | 12/2012 | Wong | |
| 2013/0197406 | A1 | 8/2013 | King et al. | |
| 2013/0278435 | A1 | 10/2013 | Ellis | |
| 2015/0068070 | A1 | 3/2015 | Moss | |
| 2017/0188850 | A1 | 7/2017 | Banet et al. | |
| 2018/0007996 | A1 * | 1/2018 | Sedwick | A43B 13/14 |
| 2018/0192739 | A1 | 7/2018 | Granger et al. | |
| 2019/0053570 | A1 | 2/2019 | Fortener | |
| 2020/0113273 | A1 | 4/2020 | Aubonnet et al. | |

OTHER PUBLICATIONS

Compere, “Flat Feet in Children.” Medical Clinics of North America, 1946, vol. 30, No. 1, 1946, pp. 147-154.

Menelaus, “Posture and Gait in Children.” The Medical Journal of Australia, Jun. 21, 1969, pp. 1312-1313.

Springer AKTIV AG, “EP3120814A1—Translation.” Jan. 25, 2017, 13 pages.

* cited by examiner

THERAPEUTIC SHOE

CROSS-REFERENCE TO RELATED APPLICATIONS

This application is a continuation of U.S. patent application Ser. No. 16/948,258, filed on Sep. 10, 2020.

BACKGROUND OF THE INVENTION

The present invention relates to footwear, and more particularly to therapeutic footwear.

Some infants/toddler/children suffer with physical and mental health disabilities, such as autism, also exhibit various biomechanical foot issues, such as pronated feet, high arches, toe walking, etc. Conventional footwear, including shoes and sneakers, do not provide the inner medial and lateral support for the ankle to correct these biomechanical foot issues and therefore do not provide for proper foot alignment at an early formation stage in their development. Children with misalignment due to various biomechanical foot issues leads to abnormality of leg development and pain.

Likewise, some children with certain mental health disabilities are also a flight risk, in that they may wander off without an awareness of their surroundings, much less with the skills necessary to find their way home, or to locate their care giver when away from home. Due to limitations of their condition, they may also run the risk of developing obesity as activity levels may be impaired or restricted.

As can be seen, there is a need for an improved footwear to correct biomechanical foot issues, to facilitate proper foot alignment at formative stages of development and a monitoring device to allow caregivers to know the whereabouts of the child's location for safety.

SUMMARY OF THE INVENTION

In one aspect of the present invention, a therapeutic footwear is disclosed. The therapeutic footwear includes a shoe body having a shoe upper, a sole attached to a bottom of the shoe body, and an interior cavity dimensioned to receive a foot of a wearer. A molded brace has a base dimensioned to conform to a bottom of the interior cavity. An aft end of the molded brace, has a cup that is dimensioned to receive a heel of the foot. A protrusion is elevated and distends from a medial and a lateral surface of an anterior portion of the cup. The protrusion is dimensioned to receive a malleolus of the foot. A sidewall extends anterior from the protrusion and is dimensioned to extend to a point adjacent to a ball of the foot. A cushioned lining is carried within the molded brace. The cushioned lining has an outer margin that extends beyond an extent of the molded brace. At least one fabric layer lines the interior cavity and is connected to the shoe upper so that the molded brace is retained within the interior cavity of the shoe body.

In some embodiments, a plurality of longitudinal metallic supports extend longitudinally along the base of the molded brace. The plurality of longitudinal metallic supports is disposed in a spaced apart relation across a width of the base.

In other embodiments, a plurality of vertical metallic supports is disposed in a spaced apart relation between the cup and the protrusion.

In other embodiments, a GPS compartment is disposed in a heel area of the sole. The GPS compartment adapted to receive a GPS tracking device.

In yet other embodiments, an access is disposed in the heel area of the sole. The access is dimensioned to install and remove the GPS tracking device from the GPS compartment.

These and other features, aspects and advantages of the present invention will become better understood with reference to the following drawings, description and claims.

DETAILED DESCRIPTION

Figure 1:
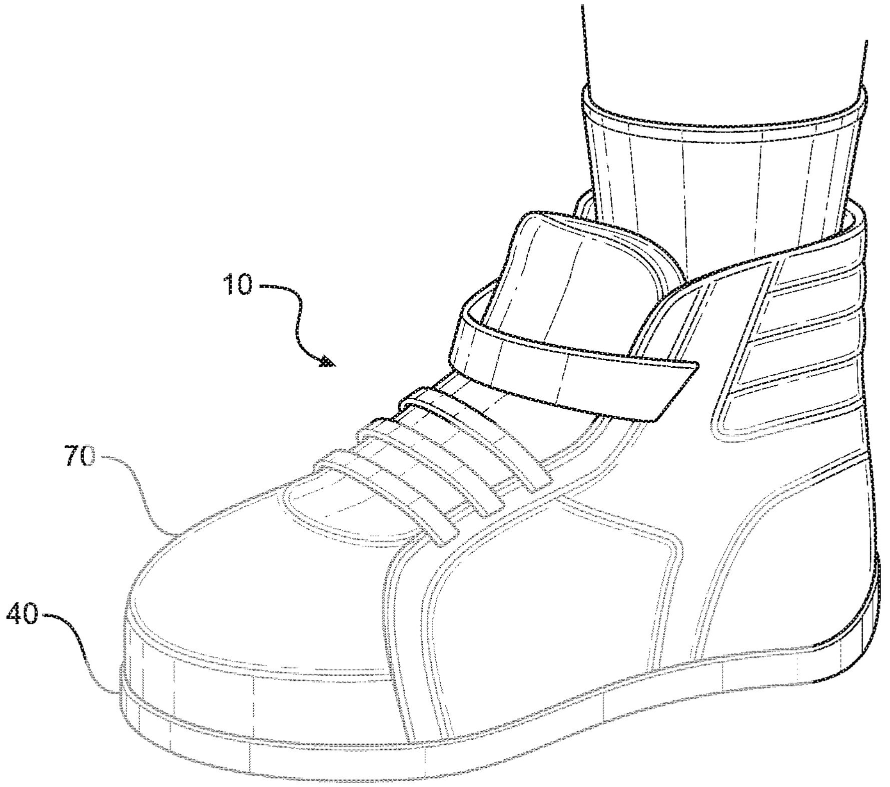
FIG. 1 is a perspective view of a high-top smart walking shoe in use.
Figure 2:
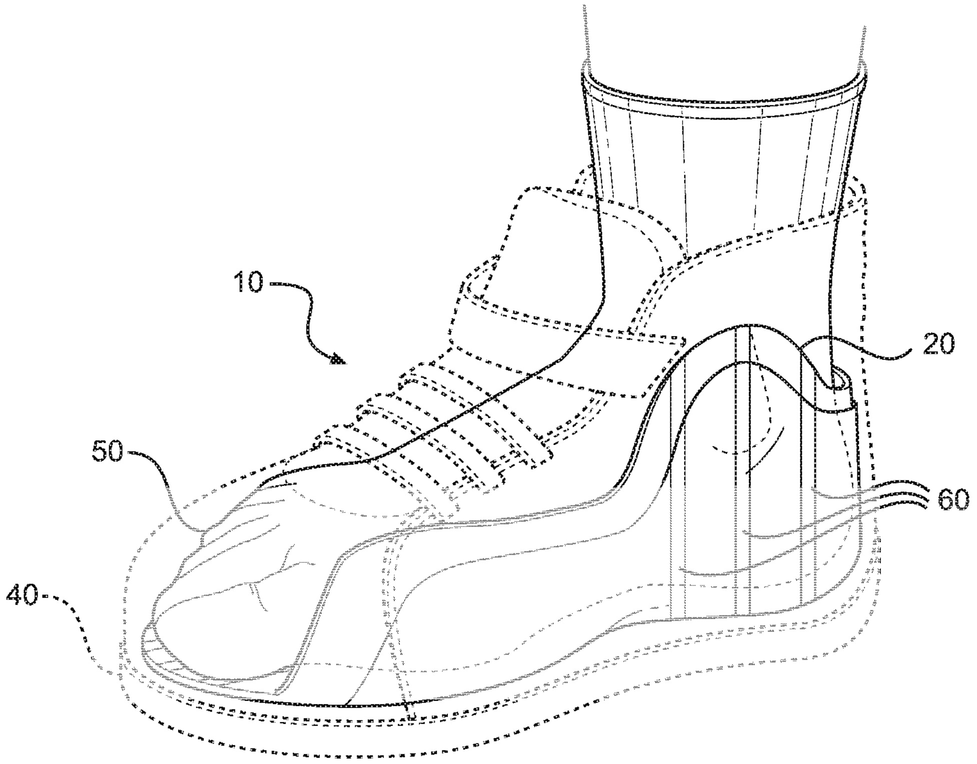
FIG. 2 is a perspective view of a high-top smart walking shoe in dash with foot resting on the molded brace inside the shoe.
Figure 3:
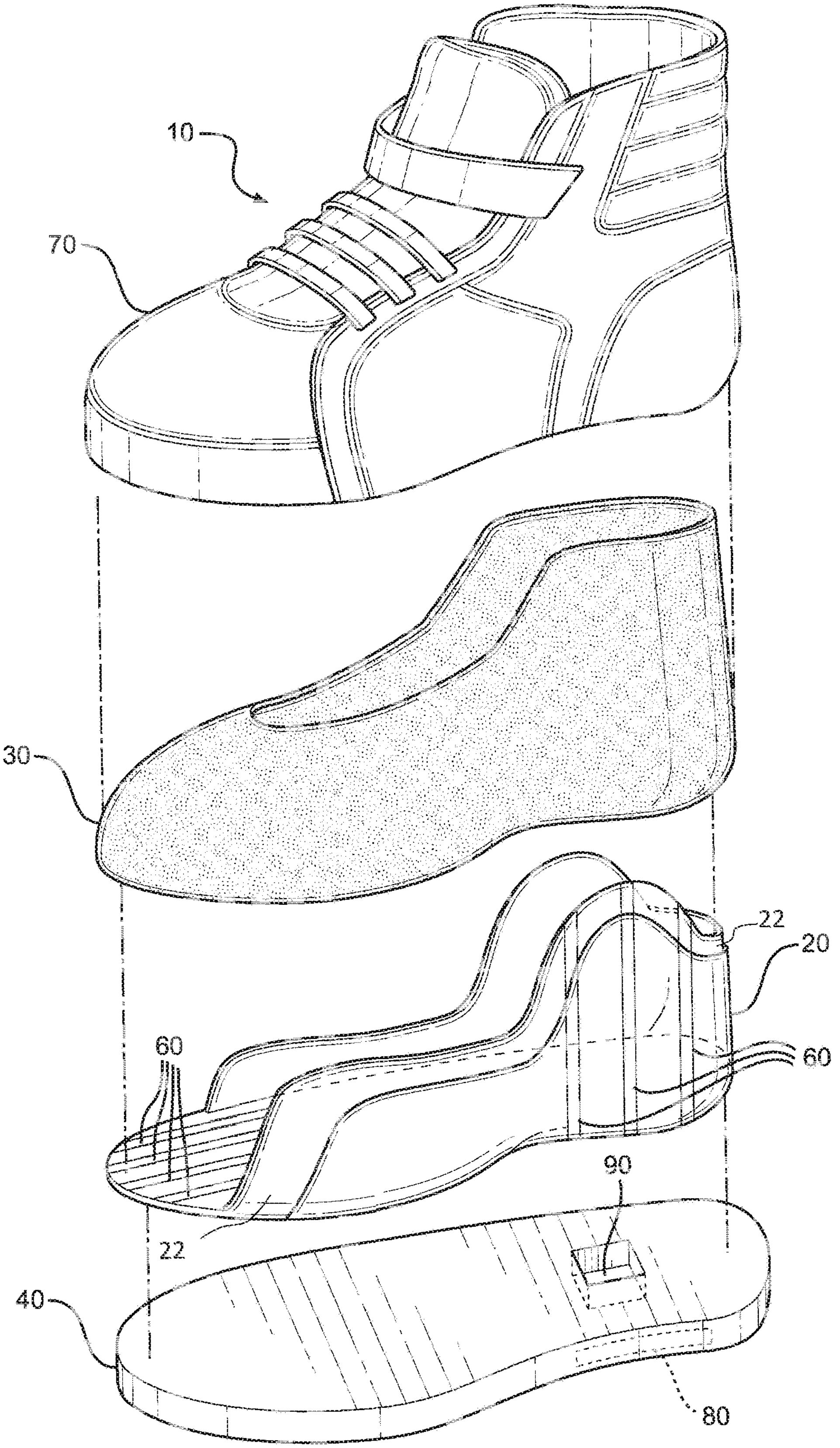
FIG. 3 is a perspective exploded view of the high-top smart walking shoe fabric covering the molded brace, and sole.

The following detailed description is of the best currently contemplated modes of carrying out exemplary embodiments of the invention. The description is not to be taken in a limiting sense, but is made merely for the purpose of illustrating the general principles of the invention.

Broadly, embodiments of the present invention provides an apparatus and method for correcting foot biomechanics in children, particularly those with physical mental disabilities, such as autism. In some embodiments, the corrective footwear includes a location tracker to facilitate locating a child that has wandered off or has become separated from a caregiver.

As seen in reference to FIGS. 1-9, a corrective therapeutic footwear according to aspects of the invention is illustrated. The corrective footwear may include a shoe body. In the non-limiting embodiment shown, the shoe body 10 may be a high-top shoe 10 that is sized according to conventional shoe sizes and dimensions. The body 10 includes a shoe upper 70 formed in the style and appearance of one of an athletic sneakers or a dress shoe. The shoe body 10 includes a sole 40 that may be formed with a rubberized athletic sole pattern or in a dress shoe pattern corresponding to the style and appearance of the shoe upper 70.

The shoe body 10 includes a molded brace 20 that is received within an interior space of the shoe body 10. The molded brace 20 may be formed with a plastic or a carbon fiber material. A cushioned lining 22 is carried within the molded brace 20 and has an outer margin that extends beyond the extents of the molded brace 20; in this manner, the cushioned lining 22 may be configured to provide a cushioning against the wearer's foot 50 and may be configured to prevent impingement of the molded brace 20 during flexing of the foot 50 and ankle within the shoe body 10. In particular, the cushioned lining 22 may lay on top of the ball of the foot 50, ensuring that the ball of the foot 50 is cushioned. The molded brace 20 includes a plurality of metallic supports 60 extending longitudinally along the base of the molded brace 20 and disposed in a spaced apart relation across a lateral width of the molded brace 20. In a preferred embodiment, the molded brace 20 is a brace which is not customized to an individual, and instead the molded brace 20 is formed for that person's age, structure, anatomical, and biomechanical size.

Figure 4:
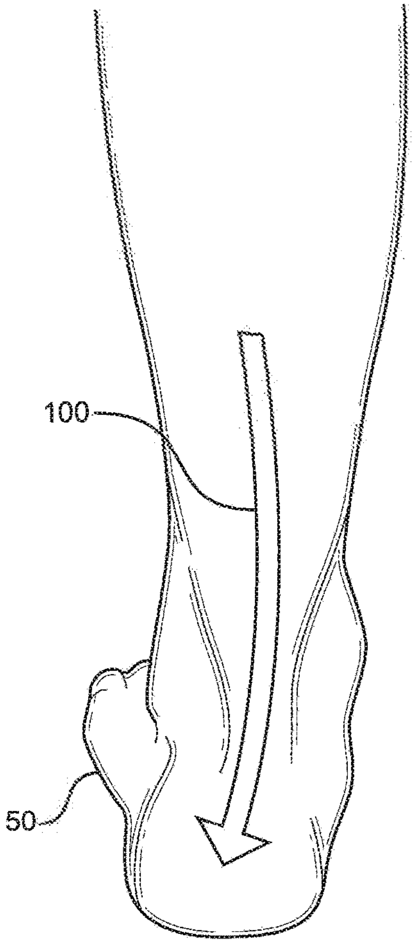
FIG. 4 is a rear view of a misaligned ankle.
Figure 5:
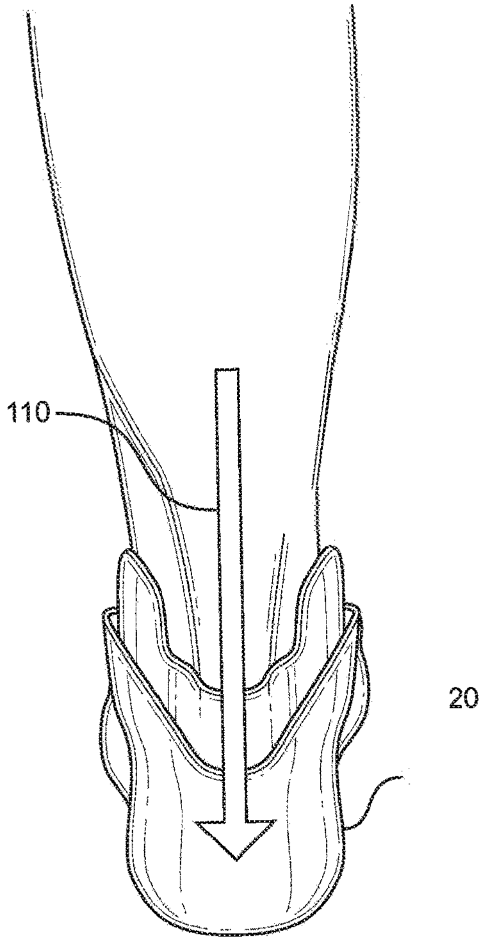
FIG. 5 is a rear view of an ankle alignment corrected by the molded brace.
Figure 6:
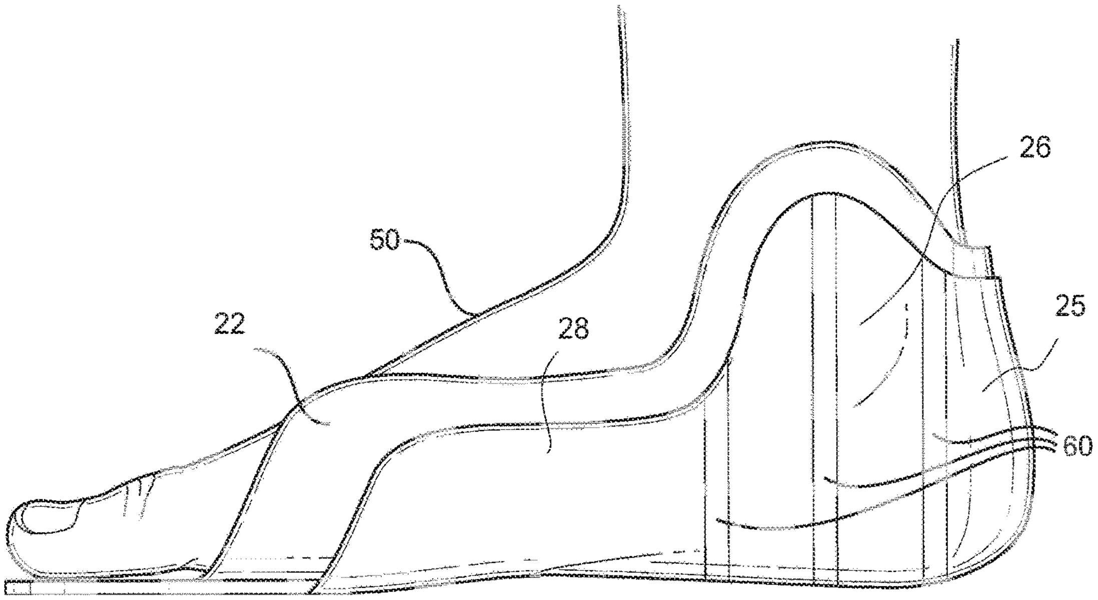
FIG. 6 is a side medial side view of the molded brace in use.
Figure 7:
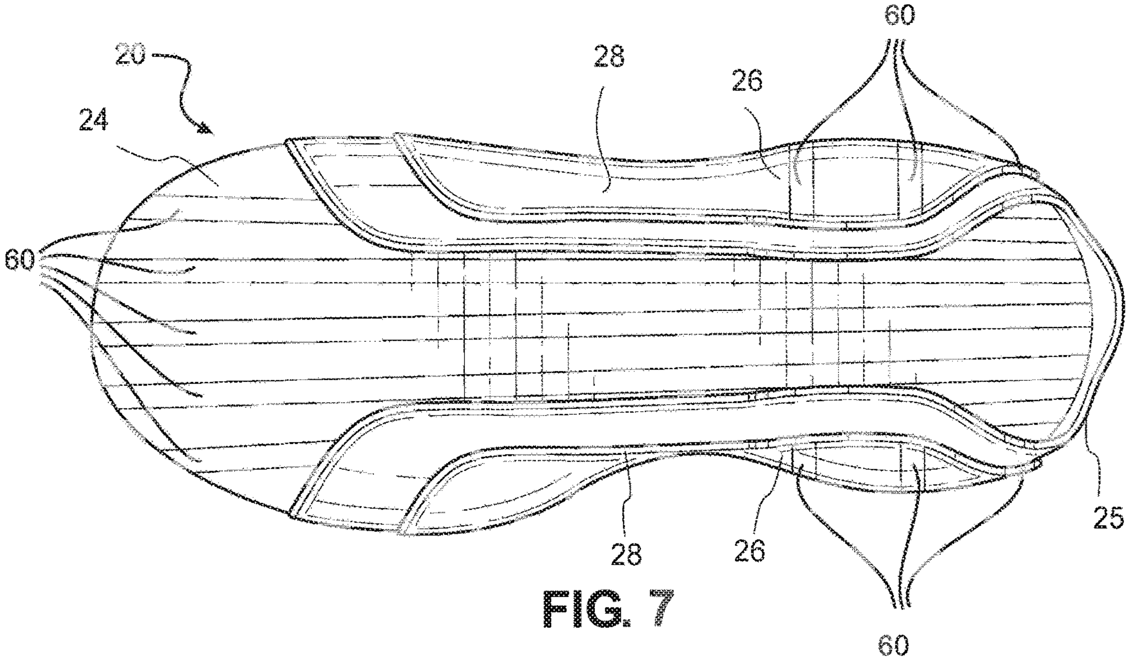
FIG. 7 is a top view of the molded brace.
Figure 8:
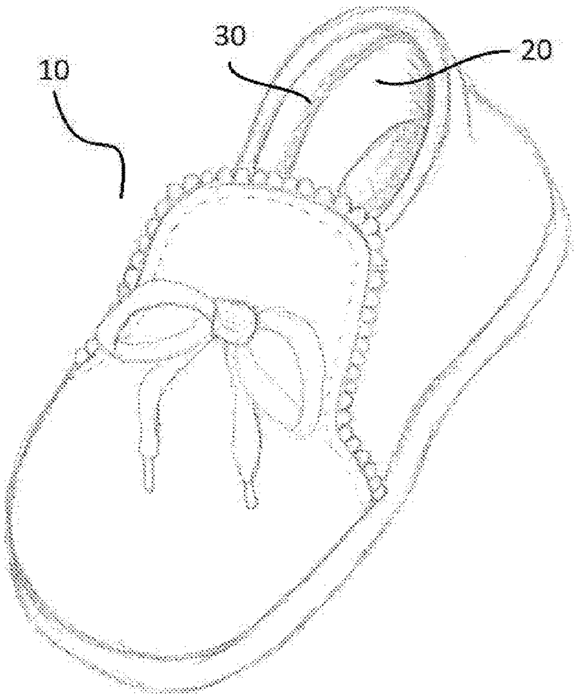
FIG. 8 is a top front perspective view of an alternative embodiment of the therapeutic shoe with the molded brace retained within the lining.
Figure 9:
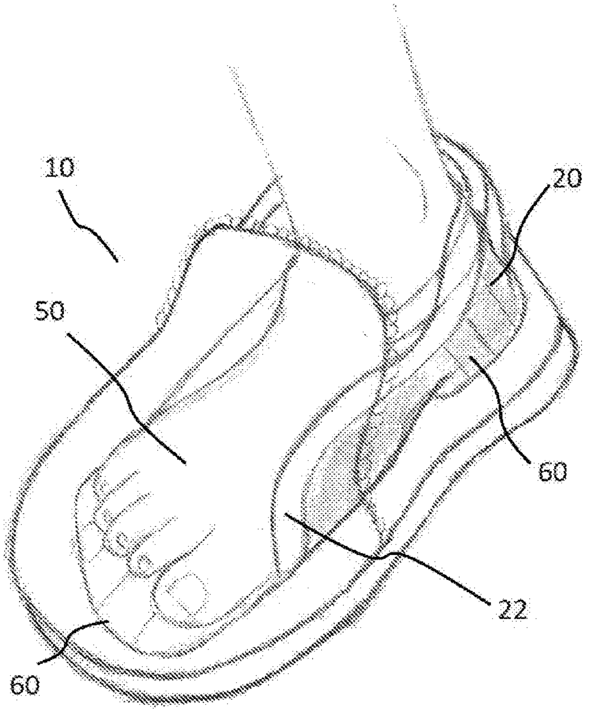
FIG. 9 is a top front perspective view of the alternative embodiment illustrating a foot and the molded brace retained under the lining.
Figure 10:
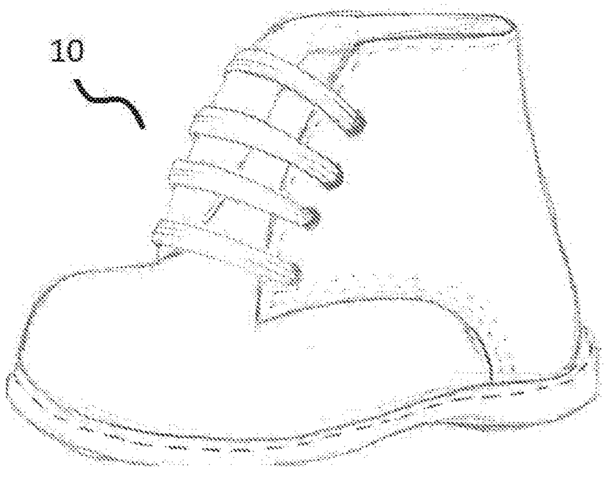
FIG. 10 is a front perspective view of another alternative embodiment of the therapeutic shoe.

As seen in reference to FIG. 4 arrow 100 is provided showing an ankle misalignment condition. Referring to FIG. 5, arrow 110 indicates a corrected alignment utilizing the shoe 10 of the present invention. The shoe body 10 with its integrated molded brace 20 and plurality of metallic supports 60 support the foot 50 just above the ankle bone or malleolus and above. The corrective therapeutic shoe 10 will support soft, flexible, flat feet (pes Plano valgus). With the incorporated molded brace 20 the shoe 10 will maintain a vertical, or neutral, heel while also supporting the arches of the foot 50 to thereby improve proper foot alignment.

The molded brace 20 is formed to correct foot alignment of the wearer. The molded brace 20 is dimensioned to fit the empty spaces on the interior of the shoe body 10 to improve fit of the posterior, medial and lateral wall of the shoe body 10 to the wearer's foot. The molded brace 20 has a base 24 that is dimensioned to conform to a bottom of the interior cavity. An aft end of the molded brace 20 has a cup 25 dimensioned to receive a heel of the foot 50. A protrusion 26 is elevated and distends from a medial and a lateral surface of an anterior portion of the cup 25. The protrusion 26 is dimensioned to receive a malleolus of the foot 50. A sidewall 28 extends anterior from the protrusion 26, for example as a unitary piece, and is dimensioned to extend to a point adjacent to a ball of the foot 50. As noted above, the cushioned lining 22 may then be carried within the molded brace 20 and have an outer margin that overlaps with the molded brace 20 and extends beyond the extents of the molded brace 20, for example overlapping with and extending beyond the extents of the protrusion 26 and the sidewall 28 of the molded brace 20, over a perimeter of the protrusion 26 and over a perimeter of the sidewall 28. The molded brace 20 reduces stress and strain on the wearer's body and bring feet 50 into proper alignment. The shoe body 10 re-align the foot 50 by re-directing and reducing certain motion to improve walking in children and may also be employed as a corrective footwear for adults.

The molded brace 20 includes a plurality of longitudinal metallic supports 60 extend longitudinally along the base 24 of the molded brace 20 and disposed in a spaced apart relation across a lateral width of the molded brace 20. A plurality of vertical metallic supports 60 are disposed in a spaced apart relation in the cup 25 and the protrusion 26. The metallic supports 60 may be embedded in the molded brace 20.

The molded brace 20 is carried within the shoe upper 70 and is covered with at least one fabric 30 layer lining an interior of the shoe body 10 so that the molded brace 20 is retained within the shoe. The at least one fabric layer 30 is attached within the interior of the shoe upper 70 to retain the molded brace 20 in position within the shoe body 10.

The sole 40 in one of a left or a right shoe may include may include a GPS compartment 90 that is dimensioned to contain a global positioning system (not shown) that is configured to provide a geographical coordinate for the location of the shoe 10, and presumably the child or person wearing the shoe 10. An access 80 may be provided to remove/install the GPS carried within the GPS compartment so that the GPS may be serviced or moved from one pair of shoes to another.

In use, the GPS carried within the GPS compartment provides geographic location information. An application may be provided to alert the parent or caregiver when the child has left a designated location. The application may also receive the geographic location information so that the parent or caregiver may locate the child, should they wander off. Likewise, the application may also activate an alarm when the geographic location information indicates that the child has departed a predetermined distance from a geographic location of the parent or care giver's mobile computing device running the application. In some embodiments, the GPS may be monitored to determine an activity level of the child to provide the caregiver guidance on exercise and eating to avoid development or for the correction of obesity.

It should be understood, of course, that the foregoing relates to exemplary embodiments of the invention and that modifications may be made without departing from the spirit and scope of the invention as set forth in the following claims.

What is claimed is:

1. A therapeutic footwear, comprising:

a shoe body having a shoe upper, a sole attached to a bottom of the shoe body, and an interior cavity dimensioned to receive a foot of a wearer;

a molded brace having a base dimensioned to conform to a bottom of the interior cavity, an aft end of the molded brace having a cup dimensioned to receive a heel of the foot, a protrusion elevated and distending from a medial and a lateral surface of an anterior portion of the cup, the protrusion dimensioned to receive a malleolus of the foot, the molded brace having a sidewall extending anterior from the protrusion as a unitary piece, and dimensioned to extend to a point adjacent to and above a ball of the foot;

a cushioned lining carried within the molded brace configured to prevent impingement of the molded brace during flexing of the foot, said cushioned lining having an outer margin overlapping with the sidewall and the protrusion that extends beyond an extent of the molded brace over a perimeter of the sidewall and over a perimeter of the protrusion;

at least one fabric layer lining the interior cavity and connected to the shoe upper so that the molded brace is retained within the interior cavity of the shoe body; and a plurality of longitudinal metallic supports continuously extending longitudinally along the base from the heel to a toe of the foot, and a plurality of parallel, vertically disposed metallic supports extending from the base of the molded brace to an upper edge of the molded brace, the supports on each side of the molded brace being disposed in equidistant, spaced apart relation along the cup and the protrusion, each vertical support being linear along an entire length thereof and terminating proximate a malleolus of the foot when the therapeutic footwear is worn.

2. The therapeutic footwear of claim 1, wherein the longitudinal metallic supports are disposed in a spaced apart relation across a lateral width of the base of the molded brace.

3. The therapeutic footwear of claim 1, wherein the longitudinal metallic supports are embedded in the base of the molded brace.

4. The therapeutic footwear of claim 1, wherein the longitudinal metallic supports extend from a rear edge of the base of the molded brace to a front edge of the base of the molded brace.

5. The therapeutic footwear of claim 1, wherein the vertical metallic supports are embedded in the cup and the protrusion.

6. The therapeutic footwear of claim 1, wherein the molded brace is disposed between the shoe upper and the fabric layer.

7. The therapeutic footwear of claim 1, wherein the fabric layer is disposed further towards the interior cavity of the shoe than the molded brace.

8. The therapeutic footwear of claim 1, further comprising:

a GPS compartment disposed in a heel area of the sole, the GPS compartment adapted to receive a GPS tracking device;

an access defined in an external surface of the heel area of the sole, the access dimensioned to install and remove the GPS tracking device from the GPS compartment; and the GPS tracking device carried within the GPS compartment.

9. A therapeutic footwear, comprising:

a shoe body having a shoe upper, a sole attached to a bottom of the shoe body, and an interior dimensioned to receive a foot of a wearer;

a molded brace received within the interior, having a cup dimensioned to receive a heel of the foot, a protrusion elevated and distending from an anterior portion of the cup, the protrusion dimensioned to receive a malleolus of the foot, the molded brace having a sidewall extending anterior from the protrusion as a unitary piece, and dimensioned to extend to a point adjacent to and above a ball of the foot;

a cushioned lining carried within the molded brace and having an outer margin that extends beyond an extent of the molded brace;

at least one fabric layer lining the interior and connected to the shoe upper so that the molded brace and the cushioned lining are retained within the interior of the shoe body; and a plurality of longitudinal metallic supports continuously extending longitudinally along a base of the molded brace from the heel to a toe of the foot, and a plurality of parallel, vertically disposed metallic supports disposed in equidistant, spaced apart relation in one or more of the cup and the protrusion, each vertical support being linear along an entire length thereof and terminating proximate a malleolus of the foot when the therapeutic footwear is worn.

10. The therapeutic footwear of claim 9, wherein the longitudinal metallic supports are disposed in a spaced apart relation across a lateral width of the base of the molded brace.

11. The therapeutic footwear of claim 9, wherein the longitudinal metallic supports are embedded in the base of the molded brace.

12. The therapeutic footwear of claim 9, wherein the longitudinal metallic supports extend from a rear edge of the base of the molded brace to a front edge of the base of the molded brace.

13. The therapeutic footwear of claim 9, wherein the vertical metallic supports extend from a height equal to a height of the base to an upper edge of the molded brace.

14. The therapeutic footwear of claim 9, wherein the vertical metallic supports are embedded in the cup and the protrusion.

15. The therapeutic footwear of claim 9, wherein:

the cushioned lining is configured to prevent impingement of the molded brace during flexing of the foot; and the outer margin of the cushioned lining overlaps with the sidewall and the protrusion, and extends over a perimeter of the sidewall and over a perimeter of the protrusion.

16. The therapeutic footwear of claim 9, wherein the molded brace is disposed between the shoe upper and the fabric layer.

17. The therapeutic footwear of claim 9, wherein the fabric layer is disposed further towards the interior of the shoe than the molded brace.

18. The therapeutic footwear of claim 9, further comprising:

a GPS compartment disposed in a heel area of the sole, the GPS compartment adapted to receive a GPS tracking device;

an access defined in an external surface of the heel area of the sole, the access dimensioned to install and remove the GPS tracking device from the GPS compartment; and the GPS tracking device carried within the GPS compartment.

19. The therapeutic footwear of claim 1, wherein the sidewall of the molded brace has an upper edge configured to extend upwardly and rearwardly from the base of the molded base adjacent to the ball of the foot, substantially horizontally along a midfoot region of the foot, curve around the malleolus of the foot at a supramalleolar region of the foot, and subsequently descend such that it is proximate an elevation of a talus at a posterior of the foot.

20. The therapeutic footwear of claim 9, wherein the sidewall of the molded brace has an upper edge configured to extend upwardly and rearwardly from the base of the molded base adjacent to the ball of the foot, substantially horizontally along a midfoot region of the foot, curve around the malleolus of the foot at a supramalleolar region of the foot, and subsequently descend such that it is proximate an elevation of a talus at a posterior of the foot.

21. A therapeutic footwear, comprising:

a shoe body having a shoe upper, a sole attached to a bottom of the shoe body, and an interior cavity dimensioned to receive a foot of a wearer;

a molded brace having a base dimensioned to conform to a bottom of the interior cavity, an aft end of the molded brace having a cup dimensioned to receive a heel of the foot, a protrusion elevated and distending from a medial and a lateral surface of an anterior portion of the cup, the protrusion dimensioned to receive a malleolus of the foot, the molded brace having a sidewall extending anterior from the protrusion as a unitary piece, and dimensioned to extend to a point adjacent to and above a ball of the foot;

a cushioned lining carried within the molded brace configured to prevent impingement of the molded brace during flexing of the foot, said cushioned lining having an outer margin overlapping with the sidewall and the protrusion that extends beyond an extent of the molded brace over a perimeter of the sidewall and over a perimeter of the protrusion;

at least one fabric layer lining the interior cavity and connected to the shoe upper so that the molded brace is retained within the interior cavity of the shoe body; and a plurality of longitudinal supports embedded in the molded brace and continuously extending longitudinally along the base from the heel to a toe of the foot, and a plurality of vertically disposed supports embedded in the molded brace and extending from an upper edge of the molded brace on one side of the molded brace, across the base, and to an upper edge of the molded brace on an opposite side of the molded brace, the supports on each side of the molded brace being disposed in spaced apart relation along the cup and the protrusion, each support being linear along an entire length thereof and terminating proximate a malleolus of the foot when the therapeutic footwear is worn.

* * * * *